US007318820B2

(12) United States Patent
LaVon et al.

(10) Patent No.: US 7,318,820 B2
(45) Date of Patent: Jan. 15, 2008

(54) SIMPLE DISPOSABLE ABSORBENT ARTICLE HAVING BREATHABLE SIDE BARRIERS

(75) Inventors: Gary Dean LaVon, Liberty Township, OH (US); Pankaj Nigam, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 309 days.

(21) Appl. No.: 10/799,947

(22) Filed: Mar. 12, 2004

(65) Prior Publication Data

US 2005/0203475 A1 Sep. 15, 2005

(51) Int. Cl.
*A61F 13/15* (2006.01)
*A61F 13/20* (2006.01)

(52) U.S. Cl. ........................... 604/385.28; 604/385.24; 604/385.25; 604/385.26; 604/385.27

(58) Field of Classification Search ................ 604/378, 604/380, 385.01, 385.04, 385.23, 385.14, 604/385.27, 393, 395, 398, 385.28
See application file for complete search history.

(56) References Cited

U.S. PATENT DOCUMENTS

| | | | |
|---|---|---|---|
| 1,733,997 | A | 10/1929 | Marr |
| 1,734,499 | A | 11/1929 | Marinsky |
| 1,989,283 | A | 1/1935 | Limacher |
| 2,058,509 | A | 10/1936 | Rose |
| 2,271,676 | A | 2/1942 | Bjornbak |
| 2,450,789 | A | 10/1948 | Frieman |
| 2,508,811 | A | 5/1950 | Best et al. |
| 2,568,910 | A | 9/1951 | Condylis |
| 2,570,796 | A | 10/1951 | Gross |
| 2,570,963 | A | 10/1951 | Mesmer |
| 2,583,553 | A | 1/1952 | Faure |
| 2,705,957 | A | 4/1955 | Mauro |
| 2,788,786 | A | 4/1957 | Dexter |

(Continued)

FOREIGN PATENT DOCUMENTS

| | | |
|---|---|---|
| EP | 0 206 208 A1 | 12/1986 |

(Continued)

OTHER PUBLICATIONS

U.S. Appl. No. 11/224,462, filed Sep. 12, 2005, LaVon et al.

*Primary Examiner*—Tatyana Zalukaeva
*Assistant Examiner*—Melanie J. Hand
(74) *Attorney, Agent, or Firm*—Michael P. Hayden; Thibault Fayette; Matthew P. Fitzpatrick

(57) ABSTRACT

A simple disposable absorbent article including an absorbent assembly attached to a chassis. The absorbent assembly includes an absorbent core that may contain superabsorbent particles, which may be contained inside pockets. The absorbent assembly is folded laterally inward at both of its side edges to form laterally opposing side flaps. Each side flap is attached to an interior surface of the absorbent assembly adjacent to its end edges. A longitudinally extending elastic gathering member is attached to each side flap adjacent to its proximal edge. When the article is worn, the elastic gathering members contract and raise the side flaps to form breathable side barriers. The chassis includes a water-impermeable sheet and may be extensible. The absorbent assembly may be attached in a cruciform pattern such that portions of the chassis that lie outside the attachment pattern are not restrained by attachment to the absorbent assembly and therefore remain extensible.

16 Claims, 10 Drawing Sheets

U.S. PATENT DOCUMENTS

| | | | |
|---|---|---|---|
| 2,798,489 | A | 7/1957 | Behrman |
| 2,807,263 | A | 9/1957 | Newton |
| 2,830,589 | A | 4/1958 | Doner |
| 2,890,700 | A | 6/1959 | Longberg-Helm |
| 2,890,701 | A | 6/1959 | Weinman |
| 2,898,912 | A | 8/1959 | Adams |
| 2,931,361 | A | 4/1960 | Sostsrin |
| 2,977,957 | A | 4/1961 | Clyne |
| 3,207,158 | A | 9/1965 | Kazuko et al. |
| 3,386,442 | A | 6/1968 | Sabee |
| 3,561,446 | A | 2/1971 | Jones |
| 3,572,342 | A | 3/1971 | Lindquist et al. |
| 3,578,155 | A | 5/1971 | Small et al. |
| 3,610,244 | A | 10/1971 | Jones |
| 3,618,608 | A | 11/1971 | Brink |
| 3,642,001 | A | 2/1972 | Sabee |
| 3,653,381 | A | 4/1972 | Warnken |
| 3,688,767 | A | 9/1972 | Goldstein |
| 3,710,797 | A | 1/1973 | Marsen |
| 3,731,688 | A | 5/1973 | Litt et al. |
| 3,756,878 | A | 9/1973 | Willot |
| 3,774,241 | A | 11/1973 | Zerkle |
| 3,776,233 | A | 12/1973 | Schaar |
| 3,814,100 | A | 6/1974 | Nystrand et al. |
| 3,840,418 | A | 10/1974 | Sabee |
| 3,847,702 | A | 11/1974 | Jones |
| 3,848,595 | A | 11/1974 | Endres |
| 3,848,597 | A | 11/1974 | Endres |
| 3,860,003 | A | 1/1975 | Buell |
| 3,882,870 | A | 5/1975 | Hathaway |
| 3,884,234 | A | 5/1975 | Taylor |
| 3,900,032 | A | 8/1975 | Heurlen |
| 3,920,017 | A | 11/1975 | Karami |
| 3,924,626 | A | 12/1975 | Lee et al. |
| 3,926,189 | A | 12/1975 | Taylor |
| 3,929,134 | A | 12/1975 | Karami |
| 3,929,135 | A | 12/1975 | Thompson |
| 3,930,501 | A | 1/1976 | Schaar |
| 3,938,523 | A | 2/1976 | Gilliland et al. |
| 3,968,799 | A | 7/1976 | Schrading |
| 3,978,861 | A | 9/1976 | Schaar |
| 3,981,306 | A | 9/1976 | Krusko |
| 3,987,794 | A | 10/1976 | Schaar |
| 3,995,637 | A | 12/1976 | Schaar |
| 3,995,640 | A | 12/1976 | Schaar |
| 3,999,547 | A | 12/1976 | Hernandez |
| 4,014,338 | A | 3/1977 | Schaar |
| 4,034,760 | A | 7/1977 | Amirsakis |
| 4,074,508 | A | 2/1978 | Reid |
| 4,084,592 | A | 4/1978 | Tritsch |
| 4,100,922 | A | 7/1978 | Hernandez |
| 4,257,418 | A | 3/1981 | Hessner |
| 4,296,750 | A | 10/1981 | Woon et al. |
| 4,315,508 | A | 2/1982 | Bolick |
| 4,324,246 | A | 4/1982 | Mullane et al. |
| 4,342,314 | A | 8/1982 | Radel et al. |
| 4,388,075 | A | 6/1983 | Mesek et al. |
| 4,461,621 | A | 7/1984 | Karami et al. |
| 4,463,045 | A | 7/1984 | Ahr et al. |
| 4,475,912 | A | 10/1984 | Coates |
| 4,490,148 | A | 12/1984 | Beckestroöm |
| 4,585,450 | A | 4/1986 | Rosch et al. |
| 4,589,878 | A | 5/1986 | Mitrani |
| 4,601,717 | A | 7/1986 | Blevins |
| 4,610,678 | A | 9/1986 | Weisman et al. |
| 4,636,207 | A | 1/1987 | Buell |
| 4,670,011 | A | 6/1987 | Mesek |
| 4,680,030 | A | 7/1987 | Coates et al. |
| 4,681,581 | A | 7/1987 | Coates |
| 4,690,680 | A | 9/1987 | Higgins |
| 4,695,278 | A | 9/1987 | Lawson |
| 4,704,115 | A * | 11/1987 | Buell .................... 604/385.26 |
| 4,704,116 | A | 11/1987 | Enloe |
| 4,731,066 | A | 3/1988 | Korpman |
| 4,747,846 | A | 5/1988 | Boland et al. |
| 4,795,454 | A | 1/1989 | Dragoo |
| 4,802,884 | A | 2/1989 | Froidh |
| 4,808,176 | A | 2/1989 | Kielpikowski |
| 4,834,735 | A | 5/1989 | Alemany et al. |
| 4,834,740 | A | 5/1989 | Suzuki et al. |
| 4,834,742 | A | 5/1989 | Wilson et al. |
| 4,838,886 | A | 6/1989 | Kent |
| 4,846,825 | A | 7/1989 | Enloe et al. |
| 4,861,652 | A | 8/1989 | Lippert et al. |
| 4,888,231 | A | 12/1989 | Angstadt |
| 4,892,528 | A | 1/1990 | Suzuki et al. |
| 4,892,536 | A | 1/1990 | Desmarais et al. |
| 4,904,251 | A | 2/1990 | Igaue et al. |
| 4,909,802 | A | 3/1990 | Ahr et al. |
| 4,909,803 | A | 3/1990 | Aziz et al. |
| 4,940,463 | A | 7/1990 | Leathers et al. |
| 4,940,464 | A | 7/1990 | Van Gompel et al. |
| 4,950,264 | A | 8/1990 | Osborn |
| 4,963,140 | A | 10/1990 | Robertson et al. |
| 4,968,313 | A | 11/1990 | Sabee |
| 4,990,147 | A | 2/1991 | Freeland |
| 5,006,394 | A | 4/1991 | Baird |
| 5,037,416 | A | 8/1991 | Allen et al. |
| 5,071,414 | A | 12/1991 | Elliott |
| 5,085,654 | A | 2/1992 | Buell |
| 5,092,861 | A | 3/1992 | Nomura et al. |
| 5,114,420 | A | 5/1992 | Igaue et al. |
| 5,135,522 | A | 8/1992 | Fahrenkrug et al. |
| D329,697 | S | 9/1992 | Fahrenkrug et al. |
| 5,151,092 | A | 9/1992 | Buell et al. |
| 5,190,606 | A | 3/1993 | Merkatoris et al. |
| 5,204,997 | A | 4/1993 | Suzuki et al. |
| 5,221,274 | A | 6/1993 | Buell et al. |
| 5,235,515 | A | 8/1993 | Ungpiyakul et al. |
| 5,246,431 | A | 9/1993 | Minetola et al. |
| 5,246,432 | A | 9/1993 | Suzuki et al. |
| 5,246,433 | A | 9/1993 | Hasse et al. |
| 5,260,345 | A | 11/1993 | DesMarais et al. |
| 5,269,775 | A | 12/1993 | Freeland et al. |
| 5,312,386 | A | 5/1994 | Correa et al. |
| 5,358,500 | A | 10/1994 | LaVon et al. |
| 5,366,782 | A | 11/1994 | Curro et al. |
| 5,387,209 | A | 2/1995 | Yamamoto et al. |
| 5,397,316 | A | 3/1995 | LaVon et al. |
| H1440 | H | 5/1995 | New et al. |
| 5,476,458 | A | 12/1995 | Glaug et al. |
| 5,518,801 | A | 5/1996 | Chappell et al. |
| 5,531,730 | A | 7/1996 | Dreier |
| 5,549,593 | A | 8/1996 | Ygge et al. |
| 5,554,145 | A | 9/1996 | Roe et al. |
| 5,569,234 | A | 10/1996 | Buell et al. |
| 5,571,096 | A | 11/1996 | Dobrin et al. |
| 5,580,411 | A | 12/1996 | Nease et al. |
| 5,584,829 | A | 12/1996 | Lavash et al. |
| 5,607,416 | A | 3/1997 | Yamamoto et al. |
| 5,607,537 | A | 3/1997 | Johnson et al. |
| 5,607,760 | A | 3/1997 | Roe |
| 5,609,587 | A | 3/1997 | Roe |
| 5,622,589 | A | 4/1997 | Johnson et al. |
| 5,624,424 | A | 4/1997 | Saisaka et al. |
| 5,625,222 | A | 4/1997 | Yoneda et al. |
| 5,626,571 | A | 5/1997 | Young et al. |
| 5,635,191 | A | 6/1997 | Roe et al. |
| 5,643,588 | A | 7/1997 | Roe et al. |
| H1674 | H | 8/1997 | Ames et al. |
| 5,662,638 | A | 9/1997 | Johnson et al. |
| 5,674,215 | A | 10/1997 | Ronnberg |
| 5,691,035 | A | 11/1997 | Chappell et al. |
| 5,691,036 | A | 11/1997 | Chappell et al. |

| | | | | |
|---|---|---|---|---|
| 5,723,087 | A | 3/1998 | Chappell et al. | |
| 5,749,866 | A | 5/1998 | Roe et al. | |
| 5,752,947 | A | 5/1998 | Awolin | |
| 5,772,825 | A | 6/1998 | Schmitz | |
| 5,779,831 | A | 7/1998 | Schmitz | |
| 5,797,894 | A | 8/1998 | Cadieux et al. | |
| 5,814,035 | A | 9/1998 | Gryskiewicz et al. | |
| 5,846,232 | A | 12/1998 | Serbiak et al. | |
| 5,851,204 | A | 12/1998 | Mitzutani | |
| 5,865,823 | A | 2/1999 | Curro | |
| 5,873,868 | A | 2/1999 | Nakahata | |
| 5,876,391 | A | 3/1999 | Roe et al. | |
| 5,891,544 | A | 4/1999 | Chappell et al. | |
| 5,897,545 | A | 4/1999 | Kline et al. | |
| 5,904,673 | A | 5/1999 | Roe et al. | |
| 5,951,536 | A | 9/1999 | Osborn, III et al. | |
| 5,957,908 | A | 9/1999 | Kline et al. | |
| 5,968,029 | A | 10/1999 | Chappell et al. | |
| 6,004,306 | A | 12/1999 | Robles et al. | |
| 6,022,430 | A | 2/2000 | Blenke et al. | |
| 6,022,431 | A | 2/2000 | Blenke et al. | |
| 6,042,673 | A | 3/2000 | Johnson et al. | |
| 6,102,892 | A * | 8/2000 | Putzer et al. | 604/385.01 |
| 6,107,537 | A | 8/2000 | Elder et al. | |
| 6,110,157 | A | 8/2000 | Schmidt | |
| 6,117,121 | A | 9/2000 | Faulks et al. | |
| 6,120,486 | A | 9/2000 | Toyoda et al. | |
| 6,120,487 | A | 9/2000 | Ashton | |
| 6,120,489 | A | 9/2000 | Johnson et al. | |
| 6,120,866 | A | 9/2000 | Aralawa et al. | |
| 6,129,720 | A | 10/2000 | Blenke et al. | |
| 6,156,424 | A | 12/2000 | Taylor | |
| 6,165,160 | A | 12/2000 | Suzuki et al. | |
| 6,174,302 | B1 | 1/2001 | Kumasaka | |
| 6,186,996 | B1 | 2/2001 | Martin | |
| 6,210,390 | B1 | 4/2001 | Karlsson | |
| 6,238,380 | B1 | 5/2001 | Sasaki | |
| 6,241,716 | B1 | 6/2001 | Ronnberg | |
| 6,322,552 | B1 | 11/2001 | Blenke et al. | |
| 6,325,787 | B1 | 12/2001 | Roe et al. | |
| 6,334,858 | B1 | 1/2002 | Ronnberg et al. | |
| 6,350,332 | B1 | 2/2002 | Thomas et al. | |
| 6,402,729 | B1 | 6/2002 | Boberg et al. | |
| 6,402,731 | B1 | 6/2002 | Suprise et al. | |
| 6,413,249 | B1 | 7/2002 | Turi et al. | |
| 6,419,667 | B1 | 7/2002 | Avalon et al. | |
| 6,432,098 | B1 | 8/2002 | Kline et al. | |
| 6,432,099 | B2 | 8/2002 | Ronnberg | |
| 6,443,933 | B1 | 9/2002 | Suzuki et al. | |
| 6,461,342 | B2 * | 10/2002 | Tanji et al. | 604/385.25 |
| 6,475,201 | B2 | 11/2002 | Saito et al. | |
| 6,494,872 | B1 | 12/2002 | Suzuki et al. | |
| 6,494,873 | B2 | 12/2002 | Karlsson et al. | |
| 6,520,947 | B1 | 2/2003 | Tilly et al. | |
| 6,524,294 | B1 | 2/2003 | Hilston et al. | |
| 6,585,713 | B1 | 7/2003 | LeMahieu et al. | |
| 6,605,070 | B2 | 8/2003 | Ludwig et al. | |
| 6,648,869 | B1 | 11/2003 | Gillies et al. | |
| 6,648,870 | B2 | 11/2003 | Itoh et al. | |
| 6,648,871 | B2 | 11/2003 | Kusibojoska et al. | |
| 6,682,515 | B1 | 1/2004 | Mizutani et al. | |
| 6,689,115 | B1 * | 2/2004 | Popp et al. | 604/385.27 |
| 6,726,792 | B1 | 4/2004 | Johnson et al. | |
| 6,880,211 | B2 | 4/2005 | Jackson et al. | |
| 6,923,797 | B2 * | 8/2005 | Shinohara et al. | 604/385.27 |
| 6,962,578 | B1 | 11/2005 | LaVon | |
| 6,972,010 | B2 | 12/2005 | Pesce et al. | |
| 6,972,012 | B1 * | 12/2005 | Pozniak et al. | 604/386 |
| 7,014,632 | B2 | 3/2006 | Takino et al. | |
| 7,037,299 | B2 | 5/2006 | Turi et al. | |
| 7,048,726 | B2 | 5/2006 | Kusagawa et al. | |
| 7,160,281 | B2 * | 1/2007 | LeMinh et al. | 604/385.22 |
| 2002/0045881 | A1 | 4/2002 | Kusibojoska et al. | |
| 2002/0087139 | A1 | 7/2002 | Popp et al. | |
| 2002/0128617 | A1 * | 9/2002 | Roe et al. | 604/367 |
| 2002/0151861 | A1 | 10/2002 | Klemp et al. | |
| 2002/0173767 | A1 | 11/2002 | Popp et al. | |
| 2003/0088223 | A1 | 5/2003 | Vogt et al. | |
| 2003/0144644 | A1 | 7/2003 | Murai et al. | |
| 2003/0148694 | A1 | 8/2003 | Ghiam | |
| 2003/0233082 | A1 | 12/2003 | Kline et al. | |
| 2004/0022998 | A1 | 2/2004 | Miyamoto et al. | |
| 2004/0082928 | A1 | 4/2004 | Pesce et al. | |
| 2004/0122411 | A1 | 6/2004 | Hancock-Cooke | |
| 2004/0147890 | A1 | 7/2004 | Nakahata et al. | |
| 2004/0162536 | A1 | 8/2004 | Ehrnsperger et al. | |
| 2004/0167486 | A1 | 8/2004 | Ehrnsperger et al. | |
| 2004/0225271 | A1 | 11/2004 | Datta et al. | |
| 2004/0236299 | A1 | 11/2004 | Tsang et al. | |
| 2004/0249355 | A1 | 12/2004 | Tanio et al. | |
| 2005/0004548 | A1 | 1/2005 | Otsubo et al. | |
| 2005/0038401 | A1 | 2/2005 | Suzuki et al. | |
| 2005/0085784 | A1 | 4/2005 | LeMinh et al. | |
| 2005/0171499 | A1 | 8/2005 | Nigam et al. | |
| 2005/0203475 | A1 | 9/2005 | LaVon et al. | |
| 2005/0288645 | A1 | 12/2005 | LaVon | |

FOREIGN PATENT DOCUMENTS

| | | | |
|---|---|---|---|
| EP | 0 403 832 | A1 | 12/1990 |
| EP | 0 893 115 | A2 | 1/1999 |
| EP | 0 916 327 | A1 | 5/1999 |
| EP | 0 951 890 | A2 | 10/1999 |
| EP | 0 793 469 | B1 | 6/2002 |
| EP | 1 224 922 | A2 | 7/2002 |
| EP | 1 447 066 | A1 | 8/2004 |
| EP | 1 447 067 | A1 | 8/2004 |
| ES | 2 213 491 | A1 | 8/2004 |
| FR | 2 566 631 | A1 | 1/1986 |
| FR | 2 612 770 | A1 | 9/1988 |
| FR | 2 810 234 | A1 | 12/2001 |
| GB | 1 307 441 | | 2/1973 |
| GB | 1 513 055 | | 6/1978 |
| GB | 2 101 468 | A | 1/1983 |
| GB | 2 262 873 | A | 7/1993 |
| JP | 04 122256 | A | 4/1992 |
| JP | EP07611942 | A2 * | 8/1996 |
| JP | 11318980 | | 11/1999 |
| WO | WO 95/29657 | A1 | 11/1995 |
| WO | WO 98/16179 | A1 | 4/1998 |
| WO | WO 99/13813 | A1 | 3/1999 |
| WO | WO 9913813 | A1 * | 3/1999 |
| WO | WO 03/009794 | A2 | 2/2003 |
| WO | WO 2004/105664 | | 12/2004 |
| WO | WO 2005/087164 | A1 | 9/2005 |
| WO | WO 2007/000315 | A1 | 1/2007 |

* cited by examiner

SIMPLE DISPOSABLE ABSORBENT ARTICLE HAVING BREATHABLE SIDE BARRIERS

FIELD OF THE INVENTION

This invention relates to disposable absorbent articles such as disposable diapers and other articles intended for use on incontinent persons.

BACKGROUND OF THE INVENTION

Disposable absorbent articles are designed to absorb and contain bodily waste in order to prevent soiling of the body and clothing of the wearer, as well as bedding or other objects with which the wearer comes into contact.

As the usage of disposable absorbent articles has expanded, their complexity has increased with the incorporation of additional features serving to enhance their performance and appearance. The costs of the materials and the costs of the manufacturing processes have also increased in conjunction with the increase in complexity. As a result, the prices at which these articles are sold have risen to levels that many potential purchasers around the world cannot afford to pay. Thus, a need exists for a simple disposable absorbent article.

SUMMARY OF THE INVENTION

The present invention provides a simple disposable absorbent article including an absorbent assembly attached to a chassis. The absorbent assembly includes an absorbent core that may contain superabsorbent particles, which may be contained inside pockets. The absorbent assembly is folded laterally inward at both of its side edges to form laterally opposing side flaps. Each side flap is attached to an interior surface of the absorbent assembly adjacent to its end edges. A longitudinally extending elastic gathering member is attached to each side flap adjacent to its proximal edge. When the article is worn, the elastic gathering members contract and raise the side flaps to form breathable side barriers. The chassis includes a water-impermeable sheet and may be extensible. The absorbent assembly may be attached to the chassis in a cruciform pattern such that portions of the chassis that lie outside the attachment pattern are not restrained by attachment to the absorbent assembly and therefore remain extensible.

BRIEF DESCRIPTION OF THE DRAWINGS

In the accompanying drawing figures, like reference numerals identify like elements, which may or may not be identical in the several exemplary embodiments that are depicted. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description.

In FIG. 1, the interior portion of the diaper 20 that faces inwardly toward the wearer and contacts the wearer is shown facing the viewer.

In FIG. 13, the interior portion of the diaper 20 that faces inwardly toward the wearer and contacts the wearer is shown facing the viewer.

In FIG. 15, the interior portion of the diaper 20 that faces inwardly toward the wearer and contacts the wearer is shown facing upward.

In FIG. 16, the absorbent assembly 200 is shown separately from a chassis 100 to which it is attached in an exemplary diaper 20 and the interior portion of the absorbent assembly 200 that faces inwardly toward the wearer and contacts the wearer is shown facing the viewer.

In FIG. 20, the section is taken at a section line corresponding to the section line 4-4 in FIG. 1.

DETAILED DESCRIPTION OF THE INVENTION

Figure 1:
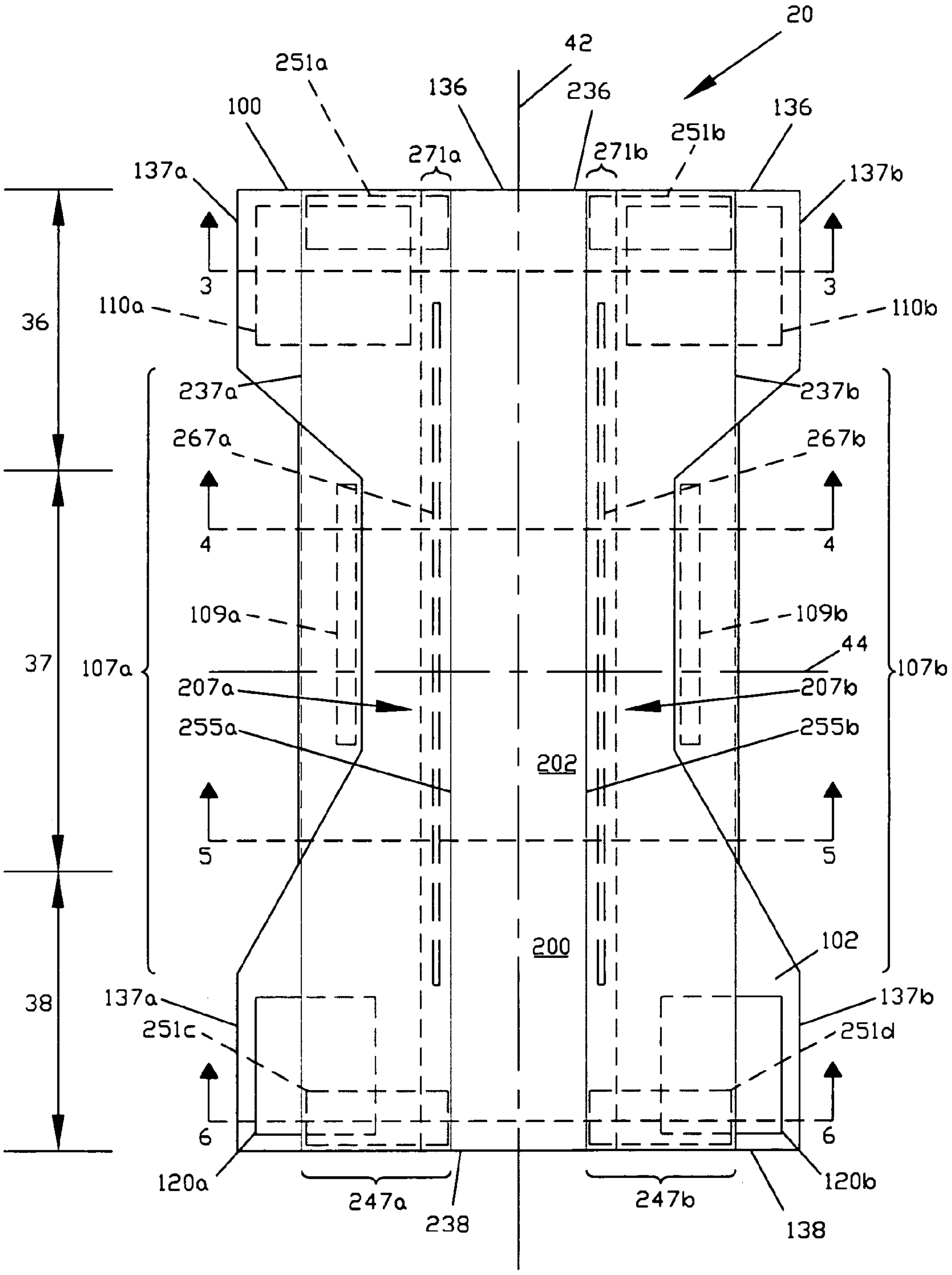
FIG. 1 is a plan view of an exemplary disposable absorbent article in the form of a diaper 20, which is shown in its flat, uncontracted state, i.e., without the contraction induced by elastic members.
Figure 2:
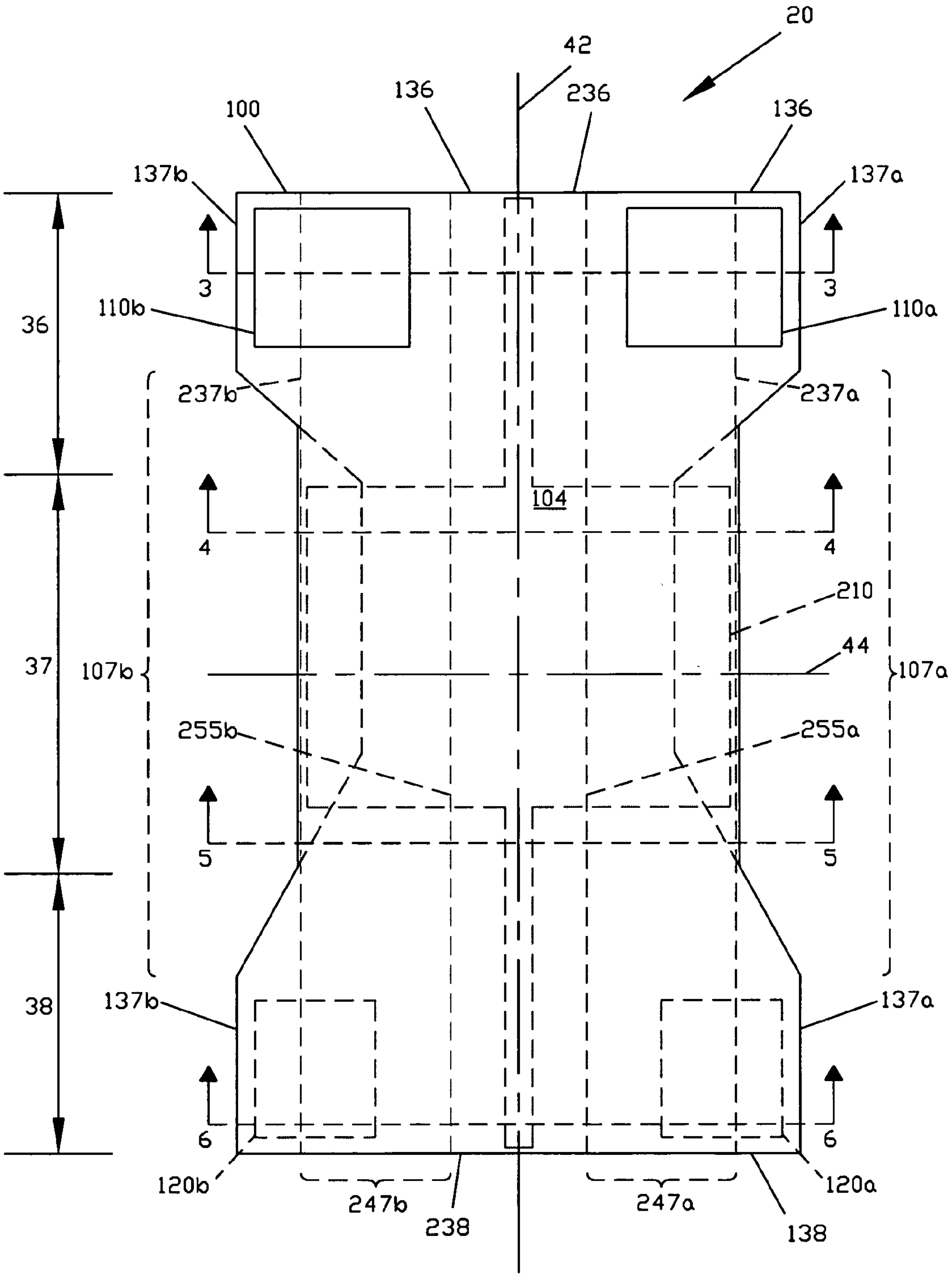
FIG. 2 is a plan view of the diaper 20 of FIG. 1 in its flat, uncontracted state, with the exterior portion of the diaper 20 that faces outwardly away from the wearer shown facing the viewer.
Figure 3:
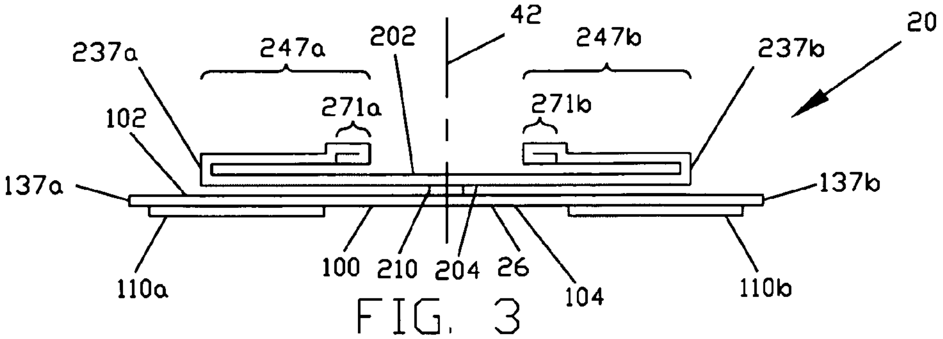
FIG. 3, FIG. 4, FIG. 5, and FIG. 6 are section views of the diaper 20 of FIG. 1 and FIG. 2 taken at the respective section lines 3-3, 4-4, 5-5, and 6-6. In these section views, the interior portion of the diaper 20 that faces inwardly toward the wearer and contacts the wearer is shown facing upward.
Figure 4:
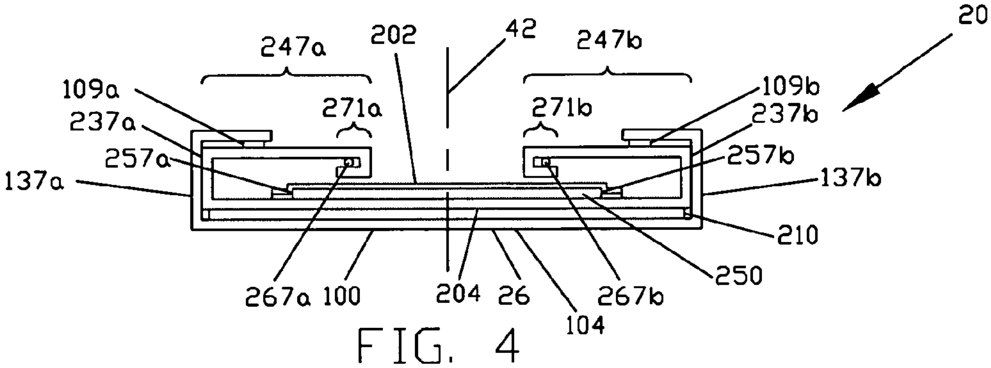
Figure 5:
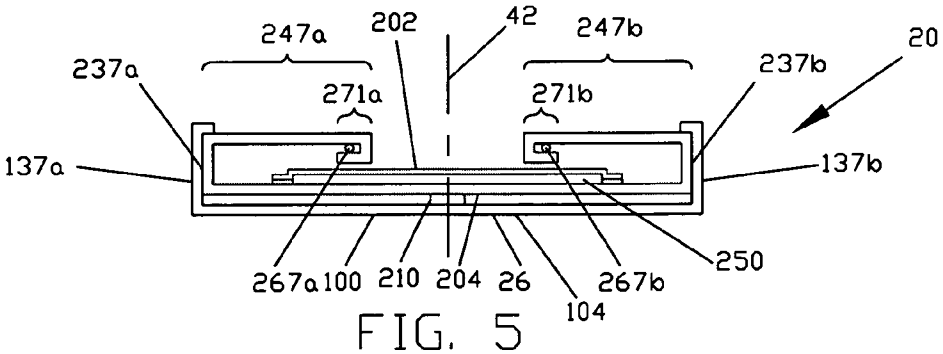
Figure 6:
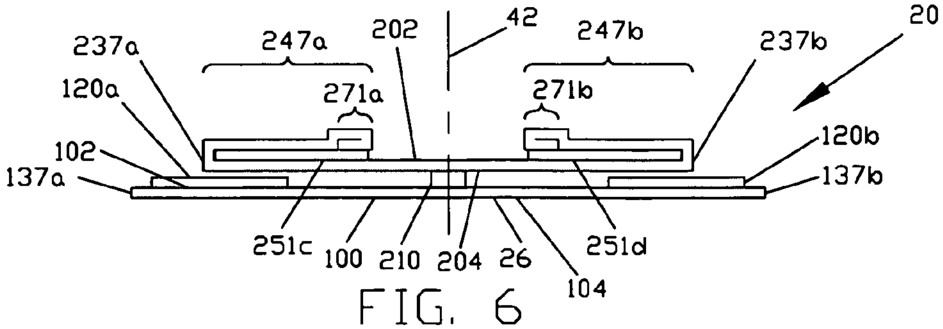

In this description, the following terms have the following meanings:

The term "absorbent article" refers to a device that absorbs and contains liquid, and more specifically, refers to a device that is placed against or in proximity to the body of the wearer to absorb and contain the various exudates discharged from the body.

The term "diaper" refers to an absorbent article that is generally worn by infants and incontinent persons about the lower torso so as to encircle the waist and the legs of the wearer and that is specifically adapted to receive and contain urinary and fecal waste.

The term "disposable" refers to the nature of absorbent articles that generally are not intended to be laundered or otherwise restored or reused as an absorbent article, i.e., they are intended to be discarded after a single use and, preferably, to be recycled, composted or otherwise disposed of in an environmentally compatible manner.

The term "longitudinal" refers to a direction running from a waist edge to an opposing waist edge of the article and generally parallel to the maximum linear dimension of the article. Directions within ±45° of the longitudinal direction are considered to be "longitudinal".

The term "lateral" refers to a direction running from a side edge to an opposing side edge of the article and generally at a right angle to the longitudinal direction. Directions within +45° of the lateral direction are considered to be "lateral".

The term "disposed" refers to an element being attached and positioned in a particular place or position in a unitary structure with other elements.

The term "attached" refers to elements being connected or united by fastening, adhering, bonding, etc. by any method suitable for the elements being attached together and their constituent materials. Many suitable methods for attaching elements together are well-known, including adhesive bonding, pressure bonding, thermal bonding, mechanical fastening, etc. Such attachment methods may be used to attach elements together over a particular area either continuously or intermittently.

The term "cohesive" refers to the property of a material that sticks to itself but does not to any significant degree stick to other materials.

The terms "water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water to pass through its thickness in the absence of a forcing pressure. Conversely, the term "water-impermeable" refers to a layer or a layered structure through the thickness of which liquid water cannot pass in the absence of a forcing pressure. A layer or a layered structure that is water-impermeable according to this definition may be permeable to water vapor, i.e., may be "water vapor-permeable". Such a water vapor-permeable layer or layered structure is commonly known in the art as "breathable". As is well known in the art, a common method for measuring the permeability to water of the materials typically used in absorbent articles is a hydrostatic pressure test, also called a hydrostatic head test or simply a "hydrohead" test. Suitable well known compendial methods for hydrohead testing are approved by INDA (formerly the International Nonwovens and Disposables Association, now The Association of the Nonwoven Fabrics Industry) and EDANA (European Disposables And Nonwovens Association).

The terms "proximal" and "distal" refer respectively to the location of an element relatively near to or far from the center of a structure, e.g., the proximal edge of a longitudinally extending element is located nearer to the longitudinal axis than the distal edge of the same element is located relative to the same longitudinal axis.

The terms "interior" and "exterior" refer respectively to the location of an element that is intended to be placed against or toward the body of a wearer when an absorbent article is worn and the location of an element that is intended to be placed against or toward any clothing that is worn over the absorbent article. Synonyms for "interior" and "exterior" include, respectively, "inner" and "outer", as well as "inside" and "outside". Also, when the absorbent article is oriented such that its interior faces upward, e.g., when it is laid out in preparation for setting the wearer on top of it, synonyms include "upper" and "lower" and "top" and "bottom", respectively.

Description of Exemplary Diaper Embodiments

As shown in FIG. 1, FIG. 2, FIG. 3, FIG. 4, FIG. 5, and FIG. 6, one end portion of the exemplary diaper 20 is configured as a front waist region 36, the longitudinally opposing end portion is configured as a back waist region 38, and an intermediate portion is configured as a crotch region 37.

The basic structure of the diaper 20 includes a chassis 100, which has a front waist edge 136, a back waist edge 138, a left side edge 137*a*, and a right side edge 137*b*, an interior surface 102, and an exterior surface 104. A longitudinal axis 42 extends through the midpoints of the front waist edge 136 and the back waist edge 138 and a lateral axis 44 extends through the midpoints of the left side edge 137*a* and the right side edge 137*b*.

The basic structure of the diaper 20 also includes an absorbent assembly 200, which has a front edge 236, a back edge 238, a left side edge 237*a*, a right side edge 237*b*, an interior surface 202, and an exterior surface 204. The absorbent assembly 200 may be disposed symmetrically or asymmetrically with respect to either or both of the longitudinal and the lateral axes. For example, the absorbent assembly 200 shown in FIG. 1 is disposed symmetrically with respect to both the longitudinal axis 42 and the lateral axis 44. The absorbent assembly 200 has laterally opposing side flaps 247*a* and 247*b* that are described in more detail below.

Figure 7:
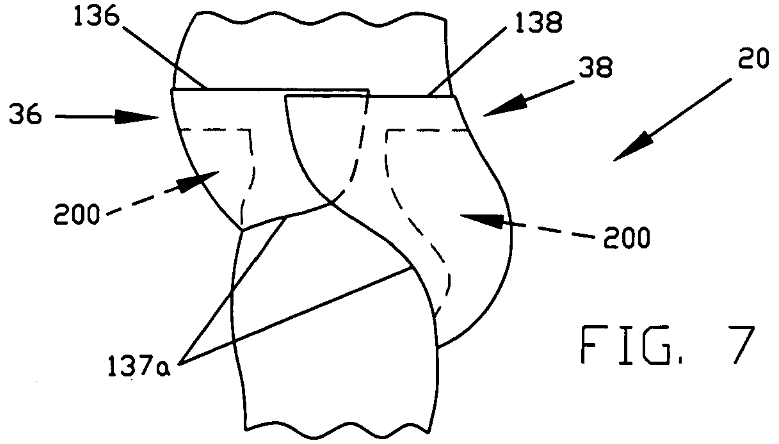
FIG. 7 is a simplified side elevation view of an exemplary diaper 20 being worn about a lower torso of a wearer.
Figure 8:
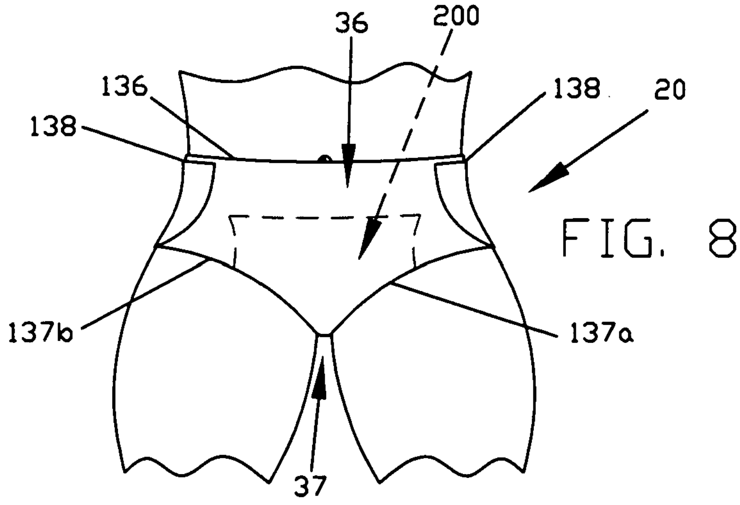
FIG. 8 is a front elevation view of the diaper 20 of FIG. 7 being worn about the lower torso of the wearer.
Figure 9:
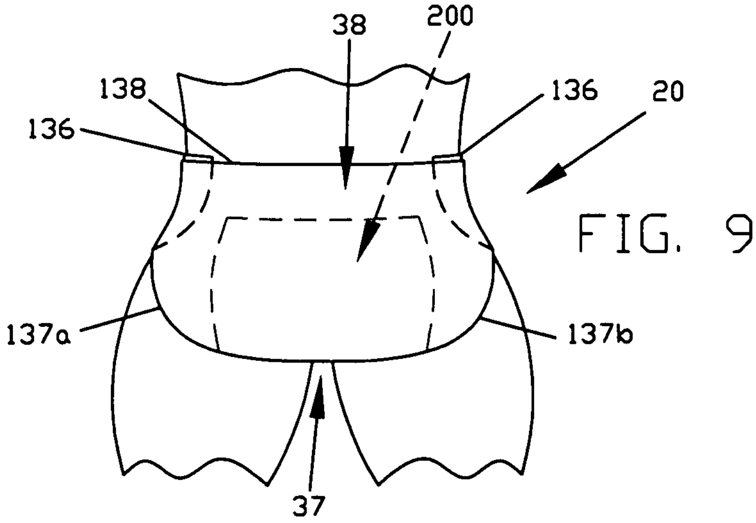
FIG. 9 is a back elevation view of the diaper 20 of FIG. 7 being worn about the lower torso of the wearer.

As shown in FIG. 7, FIG. 8, and FIG. 9, when the diaper 20 is worn on the lower torso of a wearer, the front waist edge 136 and the back waist edge 138 encircle the waist of the wearer, the chassis side edges 137*a* and 137*b* encircle the legs of the wearer, the crotch region 37 is generally positioned between the legs of the wearer, and the absorbent assembly 200 extends from the front waist region 36 through the crotch region 37 to the back waist region 38.

Description of the Chassis

The chassis 100 includes a water-impermeable backsheet 26 that is formed of a suitable material, for example a film of polyethylene or another polyolefin, or a film formed of coextruded polyolefin layers. For example, a suitable coextruded film is available from Clopay Plastic Products Co. of Mason, Ohio, U.S.A. under the designation of M18-327. A multi-layer backsheet, such as a laminate of a film and a nonwoven, may also be suitable and may be oriented with the nonwoven disposed exteriorly to provide the feel and appearance of a clot-like outermost layer, with the nonwoven disposed interiorly to separate the film from the skin of the wearer, or with nonwovens disposed both exteriorly and interiorly.

A portion or the whole of the chassis may be made extensible to a degree greater than the inherent extensibility of the material or materials from which the chassis is made.

The additional extensibility may be desirable in order to allow the chassis to conform to the body of a wearer during movement by the wearer. In particular, additional lateral extensibility may be desirable to allow the user of a diaper to extend the front waist region and/or the back waist region to encircle the waist of a wearer, i.e., to tailor the waist size and fit of a diaper to the individual wearer. Such a lateral extension of the waist region or regions may give the diaper a generally hourglass shape and may impart a tailored appearance to the diaper when it is worn. In addition, the additional extensibility may be desirable in order to minimize the cost of the diaper, because a relatively lesser amount of material is needed when the material is made extensible as described.

Figure 10:
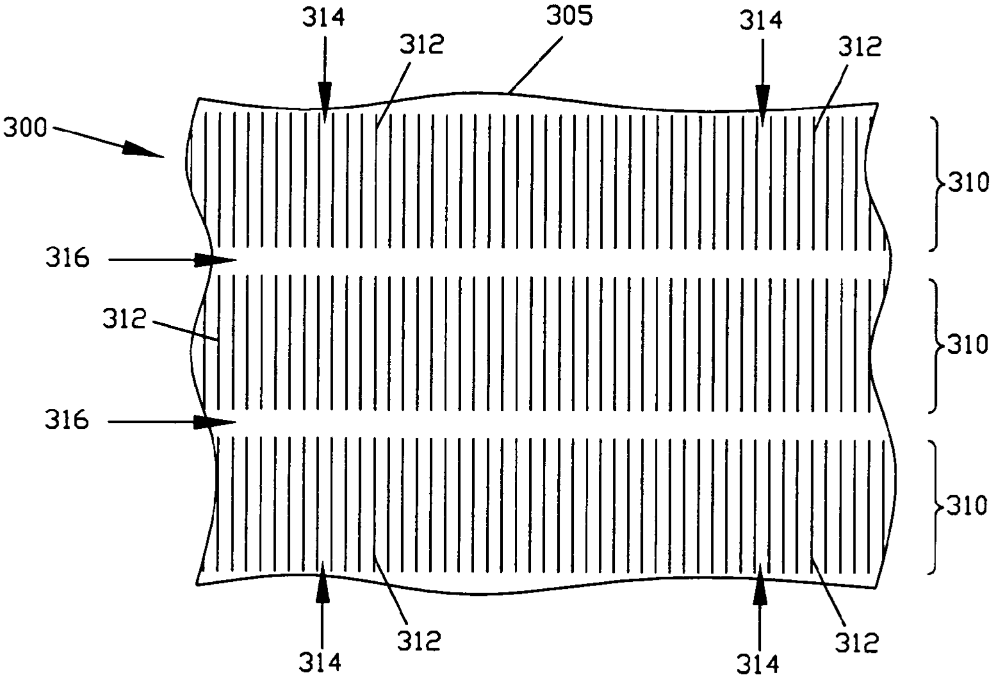
FIG. 10 is a plan view of an exemplary fragment of a formed web material.

Additional extensibility in the chassis may be provided in a variety of ways. For example, a material or materials from which the chassis is made may be pleated by any of many known methods. Alternatively, all or a portion of the chassis may be made of a formed web material or a formed laminate of web materials like those described in U.S. Pat. No. 5,518,801 issued on 21 May 1996 in the name of Chappell et al. An exemplary fragment 300 of such a formed web material 305 is shown in FIG. 10. This formed web material 305 includes distinct laterally extending regions 310 in which the original material has been altered by embossing or another method of deformation to create a pattern of generally longitudinally oriented alternating ridges 312 and valleys 314. The formed web material 305 also includes laterally extending unaltered regions 316 located between the laterally extending altered regions 310.

Such a formed web material 305 can be laterally extended beyond its original dimension with the application of relatively less force than that required to extend the same material to the same extent when undeformed. In particular, the application of opposing divergent forces directed generally perpendicular to the ridges 312 and valleys 314 extends such a formed web material along an axis between the opposing forces and generates a resistive contractive force, primarily in the unaltered regions 316. This resistive force is relatively smaller than the resistive force that is generated by the same material in its unaltered form when extended to the same extent, at least up to an extension at which the ridges and valleys in the altered regions flatten and begin to contribute to the resistive force. Thus, such formed web materials exhibit an extensible behavior resembling that of traditional elastic materials in the range of extensibility that is useful in absorbent articles, but may be made of relatively less expensive materials that are not inherently elastic and, thus, their use may provide an advantage in terms of the cost of manufacturing the absorbent articles. In addition, different portions of the chassis may be formed to have different ranges of extensibility and/or to be extensible to a greater or lesser degree when subjected to a given level of opposing tensile forces, i.e., to be relatively more easily or less easily extensible. Such differential extensibility may be desirable so that, for example, one or both of the waist regions may be laterally extended relatively farther or relatively more easily than the crotch region.

The front waist region and the back waist region can be fastened together to encircle the waist and the legs of the wearer in many ways. For example, separate fastening devices such as safety pins, separate tapes, a separate tie strap or straps, and/or a separate belt can be used for this purpose. Alternatively or in addition, fastening elements can be incorporated into the chassis to enable a user to apply the diaper to the body of the wearer without, or in conjunction with, any separate fastening devices. Many suitable types of such incorporated fastening elements are well-known, including, for example, tapes, adhesives, adhesive tape tabs, ties, buttons, hooks, loops, snap fasteners, other forms of mechanical fasteners, cohesive patches, etc. Some suitable mechanical fasteners may be adapted to engage with a nonwoven, e.g., a nonwoven layer of a laminate backsheet.

The fastening of the front waist region and the back waist region together may be openable and refastenable to allow for the adjustment of the fit of the diaper on the wearer and for the inspection of the interior of the diaper without fully removing it from the wearer. Alternatively, the fastening may be permanent, i.e., its opening may require the destruction of a portion of the diaper, e.g., the tearing of a portion of the chassis or the breaking of fused side seams.

Figure 11:
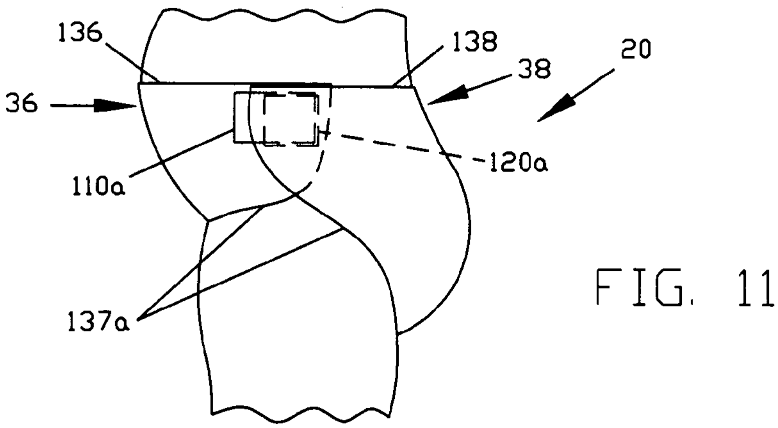
FIG. 11 is a simplified left side elevation view of an exemplary diaper 20 including cohesive fastening patches being worn about a lower torso of a wearer.
Figure 12:
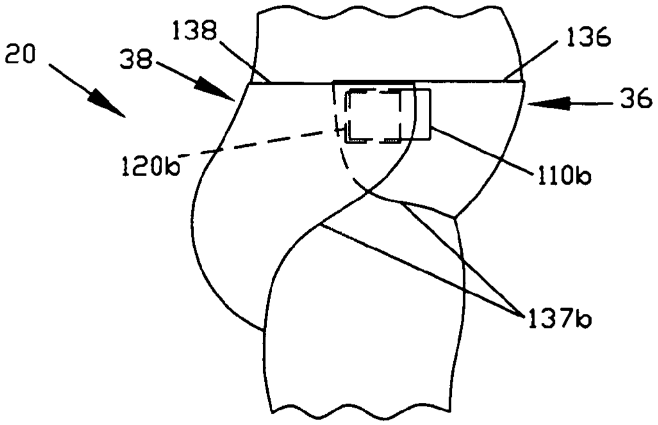
FIG. 12 is a simplified right side elevation view of the diaper 20 of FIG. 11 including cohesive fastening patches being worn about the lower torso of the wearer.

Cohesive fastening patches may be formed by the application of a cohesive material directly onto the chassis or onto a separate substrate that is in turn attached to the chassis. The cohesive material may be applied in any of a variety of patterns, such as a continuous film, discrete dots, stripes, polygons, etc., and/or spaced and interconnected geometric elements describing a grid. Suitable synthetic cohesive products are available from Andover Coated Products, Incorporated, of Salisbury, Mass. U.S.A. and are described in U.S. Pat. No. 6,156,424 issued on 5 Dec. 2000 in the name of Taylor. For example, as shown in FIG. 1, FIG. 2, FIG. 3, FIG. 6, FIG. 11, and FIG. 12, cohesive fastening patches 110*a* and 110*b* may be disposed on the exterior of the chassis 100 in the front waist region 36 and functionally complementary cohesive fastening patches 120*a* and 120*b* may be disposed on the interior of the chassis 100 in the back waist region 38. When the diaper 20 is worn as shown in FIG. 11 and FIG. 12, the cohesive fastening patches on the interior overlap the cohesive fastening patches on the exterior and the cohesion of the overlapped cohesive fastening patches fastens the front waist region 36 and the back waist region 38 together at the sides of the diaper 20. The configuration shown in these figures is adapted for back-over-front fastening. Alternatively, the front cohesive fastening patches may be disposed on the interior of the chassis and the back cohesive fastening patches may be disposed on the exterior of the chassis in order to adapt the configuration for front-over-back fastening. Alternatively, the cohesive fastening patches may be disposed in a reversible configuration that is adapted to provide the user of the diaper with both options for fastening, i.e., either back-over-front or front-over-back, according to personal preference. For example, cohesive fastening patches that are disposed on both the exterior and the interior of the chassis may allow a back cohesive fastening patch to overlap a front cohesive fastening patch or the front cohesive fastening patch to overlap the back cohesive fastening patch.

Figure 13:
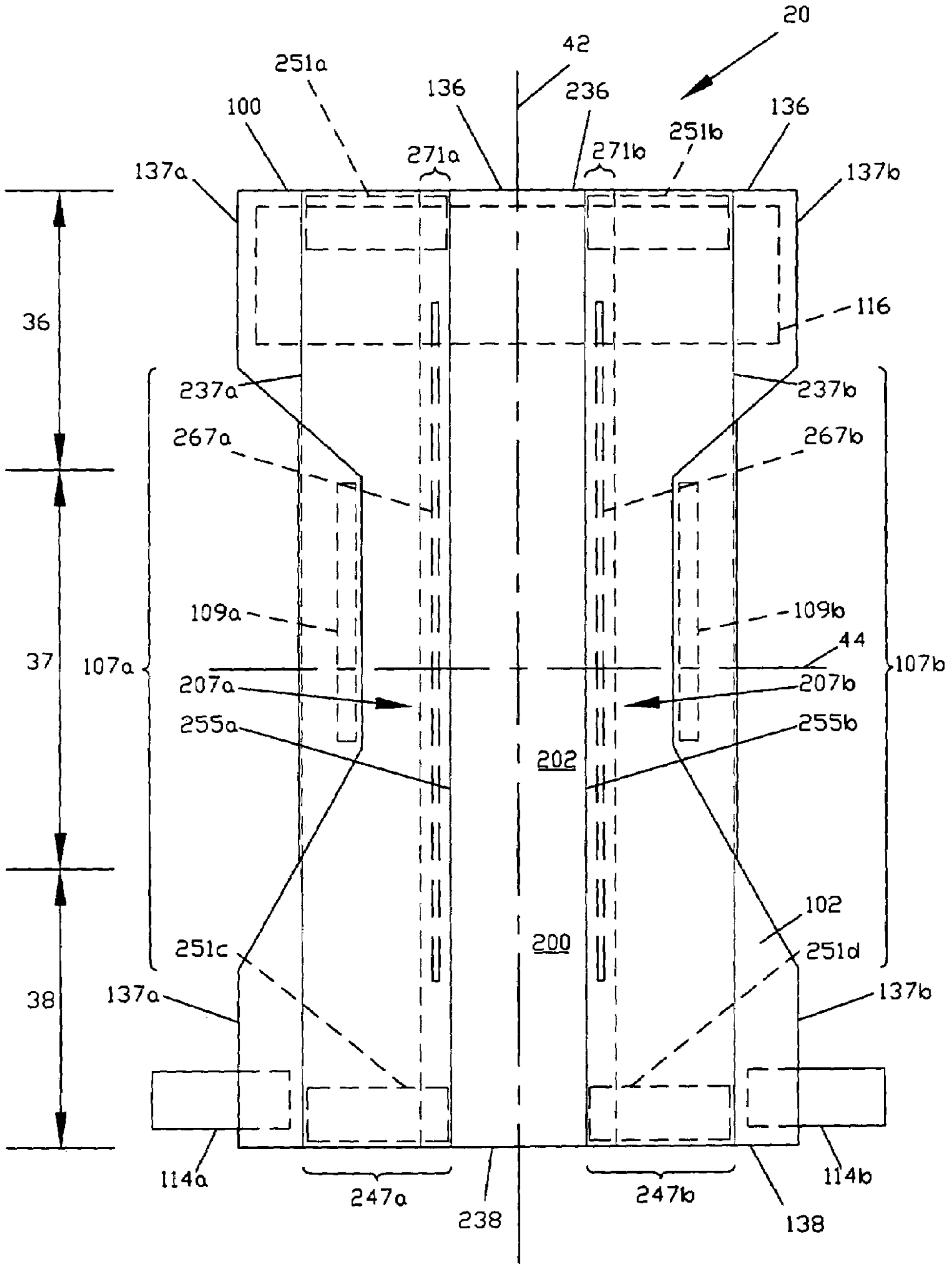
FIG. 13 is a simplified plan view of an exemplary disposable absorbent article in the form of a diaper 20, which is shown in its flat, uncontracted state, i.e., without the contraction induced by elastic members, having adhesive tape tabs 114*a* and 114*b* and a fastening surface 116 attached to the chassis.
Figure 14:
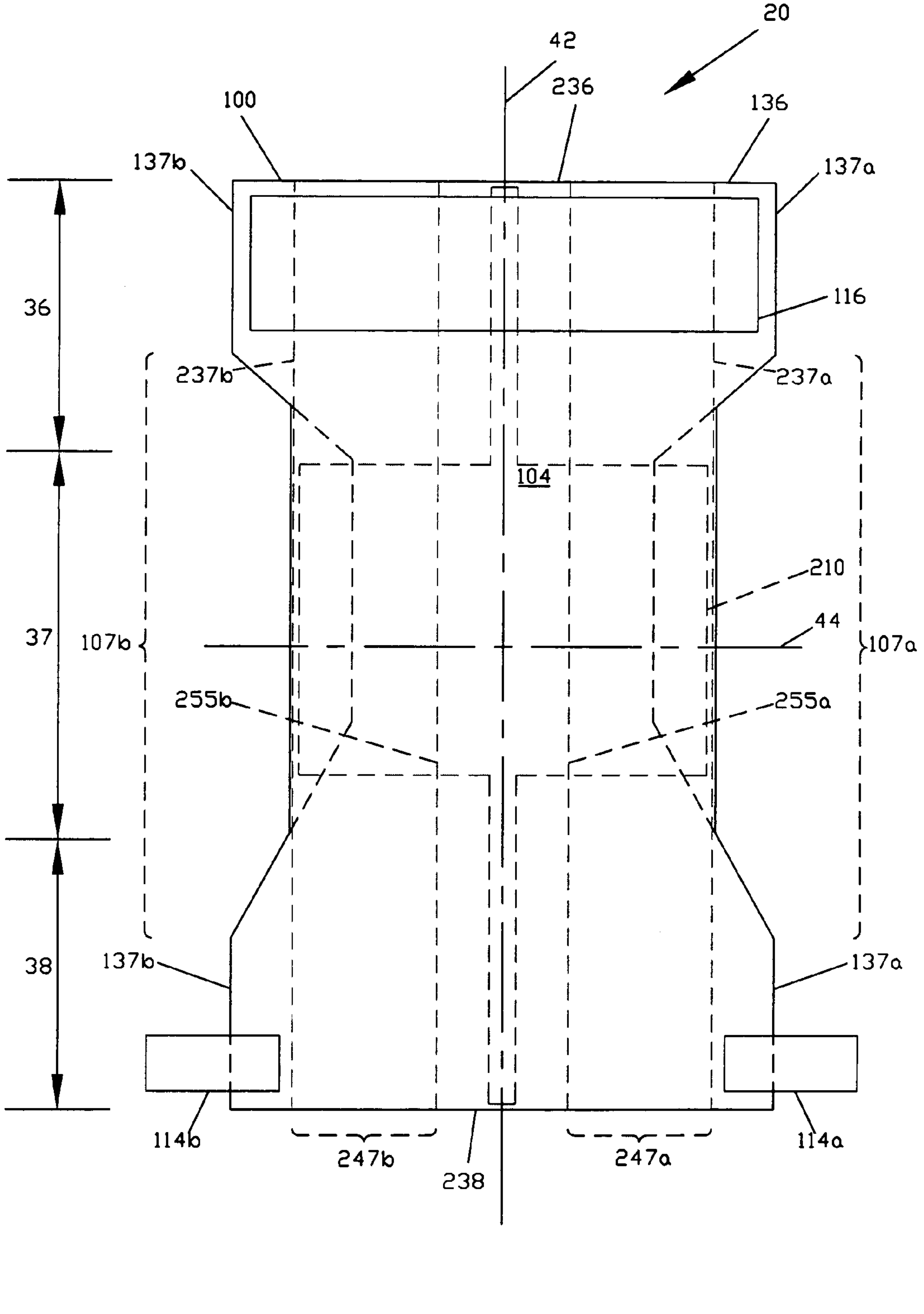
FIG. 14 is a simplified plan view of the diaper 20 of FIG. 13 in its flat, uncontracted state, with the exterior portion of the diaper 20 that faces outwardly away from the wearer shown facing the viewer.

Alternatively, as shown in FIG. 13 and FIG. 14, laterally opposing adhesive tape tabs 114*a* and 114*b* may be attached to the chassis 100 at or adjacent to the side edges 137*a* and 137*b* of the diaper 20 and may be used to fasten the back waist region 38 and the front waist region 36 together. Suitable adhesive tapes are available from the 3M Corporation of St. Paul, Minn., U.S.A., under the designation of XMF99121, and from the Avery Dennison Corporation, Specialty Tape Division, Mentor, Ohio, U.S.A., under the designation of F4416. Optionally, a fastening sheet 116 may be attached onto the exterior surface 104 of the chassis 100 as shown in FIG. 13 and FIG. 14. When a fastening sheet is provided, the adhesive tape tabs may be adhered to the fastening sheet to fasten the back waist region 38 and the front waist region 36 together. The fastening sheet serves to distribute the tensile force transmitted by each of the adhesive tape tabs over an area larger than the adhered area of the adhesive tape tab and may, itself, bear a portion of the tensile force and thereby relieve a portion of the force exerted on the backsheet. Thus, the incorporation of such a fastening sheet may make it possible to use a relatively inexpensive and relatively weak material for the backsheet. When the backsheet is extensible, it is preferable that the fastening sheet be similarly extensible such that the underlying extensible portion of the chassis is not restrained. When mechanical fasteners are used instead of adhesive tape tabs, a fastening sheet can have a surface and/or elements that engage with the mechanical fastener, e.g., loops with which hooks may engage.

Description of the Absorbent Assembly

As shown in FIG. 1, FIG. 2, FIG. 3, FIG. 4, FIG. 5, and FIG. 6, the absorbent assembly 200 has left and right laterally opposing side flaps 247*a* and 247*b*. The side flaps are formed by folding portions of the absorbent assembly toward the longitudinal axis 42, to form both the respective side flaps 247*a* and 247*b* and the side edges 237*a* and 237*b* of the absorbent assembly 200. The side flaps may overlap the absorbent core 250, i.e., the proximal edges 255*a* and 255*b* of the side flaps may lie laterally inward of the respective left side edge 257*a* and right side edge 257*b* of the absorbent core 250. Alternatively, the side flaps may not overlap the absorbent core. The side flaps are water vapor-permeable, i.e., breathable, at least in the crotch region 37 where they form side barriers when the diaper is worn, as described in detail below.

Laterally opposing portions 107*a* and 107*b* of the chassis 100 in the crotch region 37 may be folded laterally inward to overlap the respective side flaps 247*a* and 247*b* and may be attached to the side flaps, for example, in the respective attachment zones 109*a* and 109*b*. Each of the folded laterally opposing portions 107*a* and 107*b* extends laterally only a part of the way from the respective side edge 237*a* or 237*b* of the absorbent assembly 200 toward the longitudinal axis 42, thus leaving uncovered respective exposed portions 207*a* and 207*b* of the side flaps.

In the exemplary diaper 20 shown in FIG. 1, the absorbent assembly 200 extends the full length of the chassis 100 between the front waist edge 136 and the back waist edge 138. Such a full length configuration may be desirable in order to minimize the amount of waste material and the difficulty associated with the manufacture of the diaper 20, especially when the method used to manufacture the diaper 20 requires the introduction of the material or materials for the absorbent assembly 200 in the form of a continuous web or multiple continuous webs. Also, such a full length configuration may be desirable in order to isolate the skin of the wearer from the backsheet. Alternatively, the absorbent assembly 200 may be shorter and extend less than the full length of the chassis. Such a shorter configuration may be desirable in order to minimize the total amount of material used and the cost of the diaper 20.

Each of the side flaps 247*a* and 247*b* is attached to the interior surface 202 of the absorbent assembly 200 in attachment zones located at or adjacent to the front edge 236 and the back edge 238. For example, in the absorbent assembly 200 shown in FIG. 1, the left side flap 247*a* is attached to the interior surface 202 of the absorbent assembly 200 in attachment zones 251*a* and 251*c*, while the right side flap 247*b* is attached to the interior surface 202 in attachment zones 251*b* and 251*d*. The attachment zones may have equal areas or may be unequal in area. Between the attachment zones, the proximal edges 255*a* and 255*b* of the side flaps 247*a* and 247*b* remain free, i.e., are not attached to the interior surface 202 of the absorbent assembly 200.

Also between the attachment zones, each side flap preferably includes a longitudinally extensible flap elastic member that is attached adjacent to the proximal edge of the side flap. For example, in the exemplary absorbent assembly 200 shown in FIG. 1, elastic strands 267*a* and 267*b* are attached adjacent to the respective proximal edge 255*a* and 255*b* of the side flaps. The flap elastic member may be enclosed inside folded hems, such as the hems 271*a* and 271*b* shown in FIG. 4 and FIG. 5. Alternatively, the flap elastic member may be sandwiched between two layers of the absorbent assembly or may be attached on a surface of the absorbent assembly and remain exposed.

Figure 15:
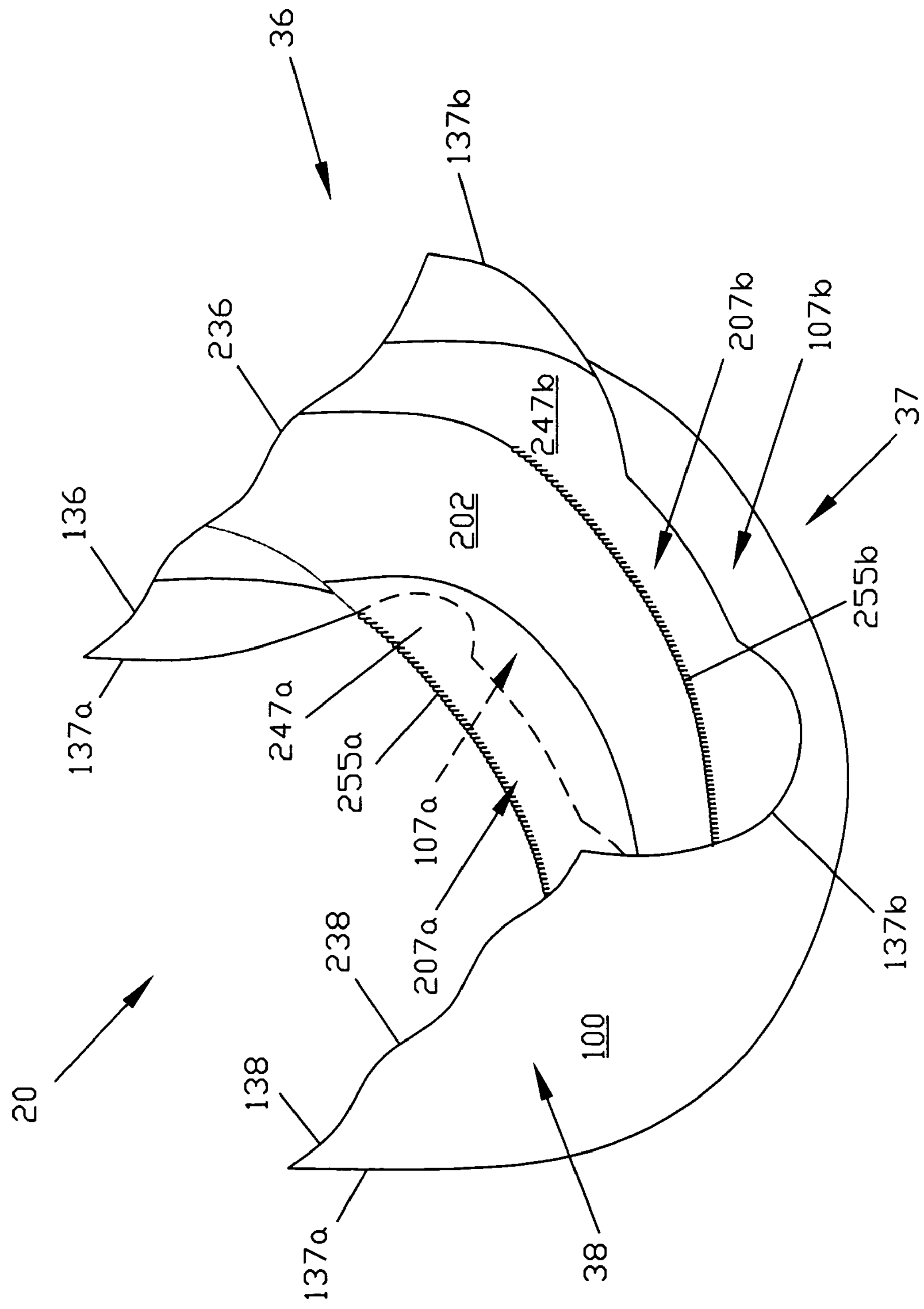
FIG. 15 is a perspective view of an exemplary diaper 20, which is shown in its relaxed, contracted state, i.e., with the contraction induced by elastic members.

When stretched, the flap elastic members allow the proximal edges of the side flaps to extend to the flat uncontracted length of the absorbent assembly, as shown in FIG. 1. When allowed to relax, the flap elastic members contract to gather the portions of the proximal edges along which the flap elastic members are attached. For example, when the exemplary diaper 20 is in a relaxed condition as shown in FIG. 15, the elastic strands 267*a* and 267*b* contract to gather the proximal edges 255*a* and 255*b* of the side flaps 247*a* and 247*b*. The contractive forces of the elastic strands pull the front waist region 36 and the back waist region 38 toward each other and thereby bend the absorbent assembly 200 and the entire diaper 20 into a "U" shape in which the interior of the "U" shape is formed by the interior portions of the diaper. Because the proximal edges remain free between the attachment zones, the contractive forces of the elastic strands lift the proximal edges 255*a* and 255*b* and the exposed portions 207*a* and 207*b* of the side flaps away from the interior surface 202 of the absorbent assembly and thereby raise the breathable side flaps into position to serve as side barriers. The lateral spacing of the lifted proximal edges is selected to allow the deposit of bodily wastes from the lower torso of the wearer into the space between the raised side flaps. The width of each of the side flaps 247*a* and 247*b* in effect becomes its height when the free portion of its proximal edge is lifted and the side flap is raised. This height preferably is selected to allow the lifted proximal edges 255*a* and 255*b* to fit into the leg creases of the body of the wearer to form seals to help prevent the leakage of deposited bodily waste out of the diaper.

The absorbent assembly may be attached to the chassis over any part or the whole of the area of the absorbent assembly. Preferably, the absorbent assembly is attached on its exterior surface to the chassis in a cruciform attachment pattern, i.e., in an attachment pattern that forms or is arranged in a cross or "+" shape. The cruciform attachment pattern may be contiguous, i.e., all of its portions may be touching or connected throughout the pattern in an unbroken sequence, or may include detached portions and thereby lack contiguity but still be arranged such that the shape of the overall pattern is a cruciform. An exemplary contiguous cruciform attachment pattern 210 is shown in FIG. 2, FIG. 14, FIG. 16, FIG. 17, and FIG. 18. When an adhesive is used for the attachment, less may be necessary in a cruciform attachment pattern than in a more extensive attachment pattern. In addition, the portions of the chassis that lie outside such a cruciform attachment pattern are not restrained by attachment to the absorbent assembly and therefore remain extensible. In particular, a relatively narrow longitudinally extending portion 212 of a cruciform attachment pattern 210 like that shown in FIG. 16 and FIG. 18 leaves the majority of the width of the chassis 100 in the front waist region 36 and in the back waist region 38 freely extensible and thereby allows extension of the chassis 100 in the lateral direction in these regions. A relatively wide laterally extending portion 214 of a cruciform attachment pattern 210 like that shown in FIG. 16 and FIG. 17 prevents the portion of the chassis 100 in the crotch region 37 to which the absorbent assembly 200 is attached from shifting relative to the absorbent assembly 200 in that region and thereby contributes to the effectiveness of the raised side flaps. For example, if the chassis in the crotch region 37 were free to shift laterally such that the left side edge 137*a* and/or the right side edge 137*b* moved toward the longitudinal axis 42, the raised side flaps 247*a* and 247*b* might distort and fail to maintain contact with the body or become improperly positioned.

Within the extent of the cruciform attachment pattern, the absorbent assembly may be attached to the chassis continuously or intermittently. For example, a film of an adhesive may be applied continuously over the entire area of the cruciform attachment pattern and then used to continuously attach the absorbent assembly to the chassis. As an alternative example, an adhesive may be applied discontinuously at and inside the boundaries of the cruciform attachment pattern, such as in the form of dots, stripes, beads, spirals, etc., and then used to attach the absorbent assembly to the chassis.

Figure 16:
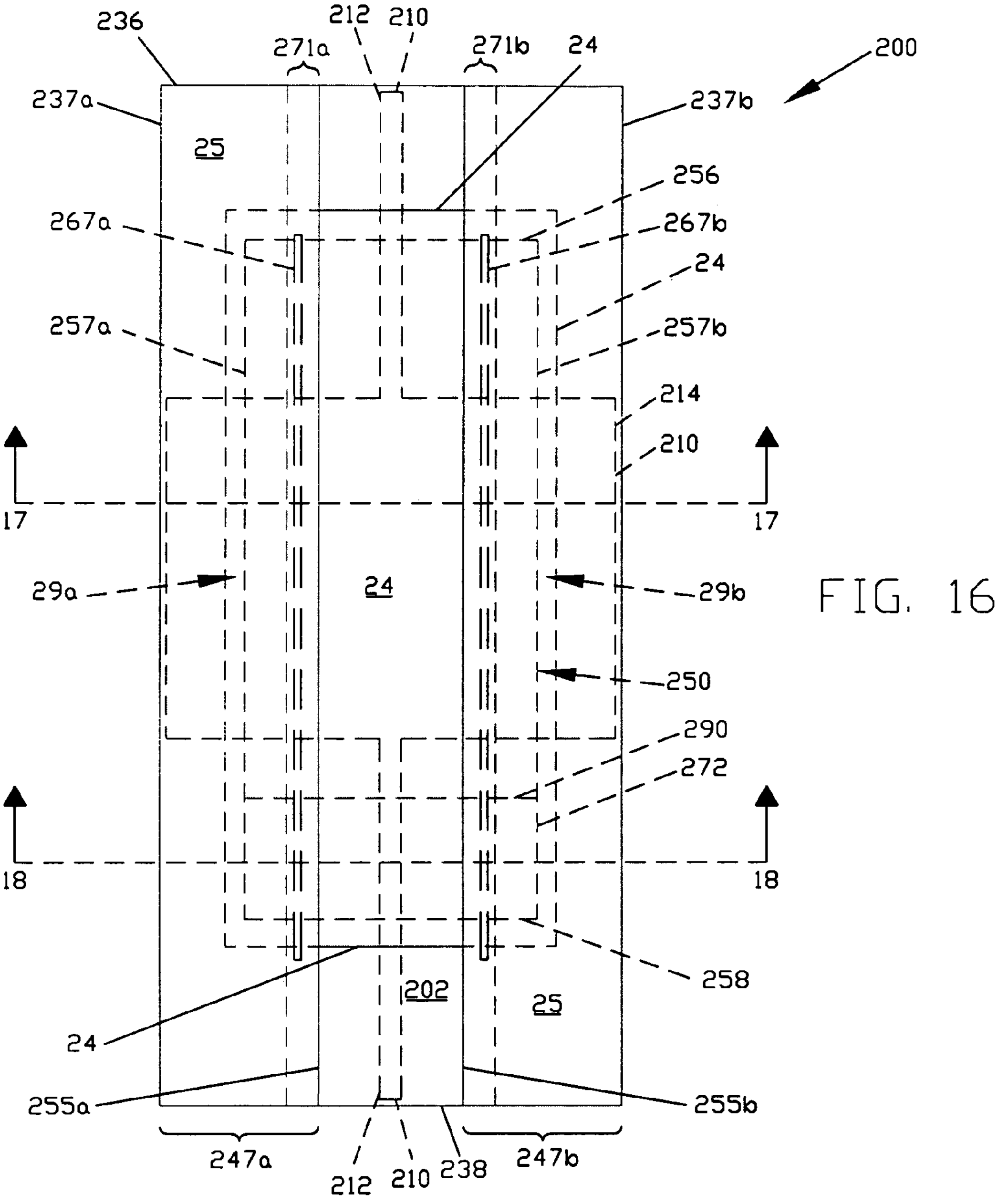
FIG. 16 is a plan view of an exemplary absorbent assembly 200.
Figure 17:
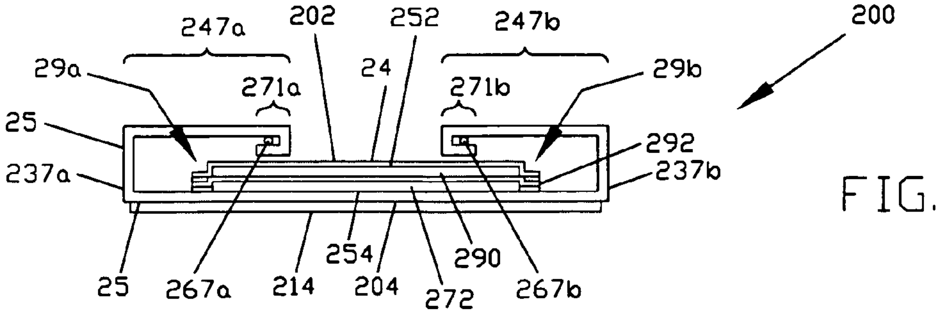
FIG. 17 is a section view of the absorbent assembly 200 of FIG. 16 taken at the section line 17-17.
Figure 18:
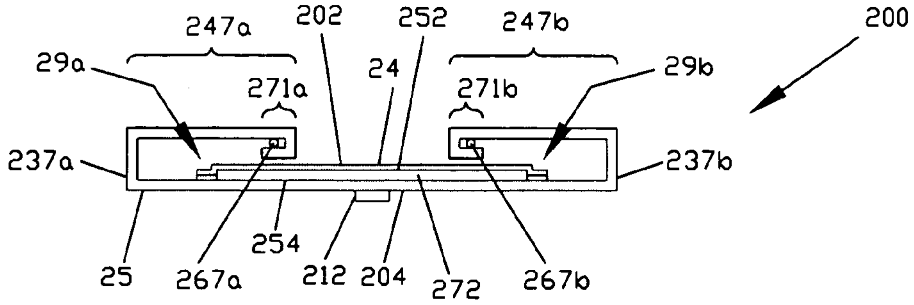
FIG. 18 is a section view of the absorbent assembly 200 of FIG. 16 taken at the section line 18-18.

As shown in FIG. 16, FIG. 17, and FIG. 18, the absorbent assembly 200 includes an absorbent core 250 that serves to absorb and retain liquid bodily waste materials. The absorbent core 250 has a front edge 256, a back edge 258, a left side edge 257*a*, a right side edge 257*b*, an interior surface 252, and an exterior surface 254.

The absorbent core 250 includes a storage component 272 that serves to absorb and retain liquid bodily waste materials. Suitable known materials for the absorbent core storage component include cellulose fibers in the form of comminuted wood pulp, which is commonly known as "airfelt", layers or sheets of a natural or synthetic fibrous material or materials, a superabsorbent polymer or polymers, etc. These absorbent materials may be used separately or in combination. Many known absorbent materials may be used in a discrete form, i.e., in the form of fibers, granules, particles, and the like. Such a discrete form of an absorbent material may be immobilized by an adhesive that attaches the discrete pieces together to form a coherent layer or that attaches the discrete pieces to a substrate layer or that attaches the discrete pieces both to each other and to the substrate layer.

The absorbent core may include an acquisition component in addition to one or more storage components. The absorbent core acquisition component serves to acquire deposited liquid bodily waste material and transfer it to the absorbent core storage component. Any porous absorbent material which will imbibe and partition liquid bodily waste material to the storage component or components may be used to form the acquisition component. Preferred materials for the acquisition component include synthetic fiber materials, open celled polymeric foam materials, fibrous nonwoven materials, cellulosic nonwoven materials, and various combination synthetic/cellulosic nonwoven materials. For example, the acquisition component may be formed of a nonwoven web or webs of synthetic fibers including polyester, polypropylene, and/or polyethylene, natural fibers including cotton and/or cellulose, blends of such fibers, or any equivalent materials or combinations of materials. Examples of such acquisition materials are more fully described in U.S. Pat. No. 4,950,264 issued to Osborn on Aug. 21, 1990. High loft nonwoven acquisition materials suitable for the acquisition component of the present invention can be obtained from Polymer Group, Inc., (PGI), 450 N.E. Blvd, Landisville, N.J. 08326, U.S.A., under the material code designation of 98920.

Such an absorbent core acquisition component 290 is shown overlying the absorbent core storage component 272 in FIG. 16, FIG. 17, and FIG. 18. A separation sheet 292 of, e.g., a tissue or a nonwoven material, may be disposed between the absorbent core storage component 272 and the absorbent core acquisition component 290 to help ensure that none of the gel formed by a superabsorbent polymer reaches the skin of the wearer. This separation sheet may extend laterally beyond the side edges of the absorbent core and the upper covering sheet may be attached to the separation sheet, which in turn may be attached to the lower covering sheet, rather than the upper covering sheet and the lower covering sheet being attached directly to each other. In this arrangement, the liquid bodily waste materials that is deposited onto the upper covering sheet 24 will pass through the thickness of the upper covering sheet 24 to be absorbed by the absorbent core acquisition component 290, and some or all of it may then pass through the thickness of the separation sheet 292 and then be absorbed and retained by the absorbent core storage component 272.

The absorbent assembly 200 may include an upper covering sheet that is disposed in a face-to-face arrangement with the interior surface 252 of the absorbent core 250 and/or a lower covering sheet that is disposed in a face-to-face arrangement with the exterior surface 254 of the absorbent core 250 and the interior surface 102 of the chassis 100. If both are present, such an upper covering sheet and lower covering sheet may be attached together to contain the absorbent core 250 between them and thereby form the absorbent assembly 200. For example, in the exemplary absorbent assembly 200 shown in FIG. 16, FIG. 17, and FIG. 18, an upper covering sheet 24 and a lower covering sheet 25 are attached together at or adjacent to the side edges 237*a* and 237*b* of the absorbent assembly 200 in attachment zones 29*a* and 29*b*. Both the upper covering sheet and the lower covering sheet are water vapor-permeable, i.e., breathable.

The upper covering sheet is water-permeable and allows liquid bodily waste to pass through its thickness to the absorbent core. The upper covering sheet preferably is formed of a soft material that will not irritate the skin of the wearer, for example a synthetic nonwoven such as spunbonded or carded polypropylene, polyester, or rayon. The lower covering sheet is water-impermeable. The lower covering sheet may be formed of any suitable material that is formed or treated to be breathable, for example the same material as the backsheet, a polyolefinic film, a microporous breathable film, or a hydrophobic nonwoven.

The upper covering sheet and the lower covering sheet may extend to the same width and the same length. Alternatively, one or more of the edges of one of the covering sheets may lie distally relative to the respective edge or edges of the other covering sheet. For example, the upper covering sheet may extend longitudinally only to an extent sufficient to cover the absorbent core and to be attached to the lower covering sheet adjacent to either the front or the back edge of the absorbent core, while the lower covering sheet may extend longitudinally beyond the upper covering sheet toward or to the adjacent waist edge of the chassis. Such a longitudinally extended lower covering sheet may serve to isolate the skin of the wearer from a portion of the backsheet as may be desirable, for example, when the diaper is worn under conditions in which contact between the skin and a backsheet film could be uncomfortable. Similarly, the upper covering sheet may extend laterally only to an extent sufficient to cover the absorbent core and to be attached to the lower covering sheet adjacent to either the left or the right side edge of the absorbent core and the lower covering sheet may extend laterally beyond the upper covering sheet. For example, in the exemplary absorbent assembly 200 shown in FIG. 16, FIG. 17, and FIG. 18, the upper covering sheet 24 extends laterally only a relatively small distance beyond the side edges 257*a* and 257*b* of the absorbent core 250 and is attached to the lower covering sheet 25 in this area. The lower covering sheet 25 in this exemplary absorbent assembly extends laterally beyond the upper covering sheet 24 and is folded to form the side flaps 247*a* and 247*b*.

Figure 19:
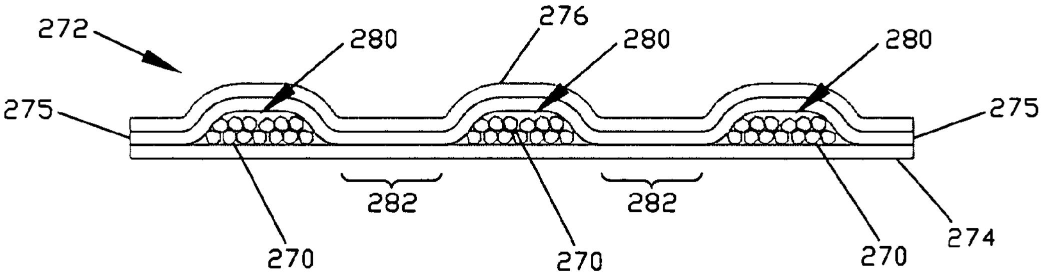
FIG. 19 is a section view of an exemplary absorbent assembly 200 showing details of an exemplary absorbent core having particles of superabsorbent material contained inside pockets

As shown in FIG. 19, in some exemplary embodiments, an absorbent core storage component 272 may include the discrete form of an absorbent material that is immobilized in pockets formed by a layer of a thermoplastic material, such as a hot melt adhesive, that intermittently contacts and adheres to a substrate sheet, while diverging away from the substrate sheet at the pockets. Absorbent core components having such structures and being suitable for the storage of liquid bodily wastes are described in co-pending and commonly assigned European Patent Applications Nos. 03 002 678.5 and 03 002 677.7, both filed on 12 Feb. 2003, and in co-pending and commonly assigned U.S. patent applications Ser. Nos. 10/776,839, published as U.S. Patent Application Publication No. 2004/0167486 on 26 Aug. 2004, and 10/776,851, published as U.S. Patent Application Publication No. 2004/0162536 on 19 Aug. 2004, both filed with respective priority claims to the aforementioned European Applications. An exemplary absorbent core storage component 272 having such a structure is shown in FIG. 19. In this absorbent core storage component 272, particles 270 of a superabsorbent polymer are contained inside pockets 280 formed by a layer 275 of a thermoplastic material. The absorbent core storage component may include both particles of a superabsorbent polymer and airfelt and both materials may be contained inside the pockets formed by the layer of the thermoplastic material. Alternatively, as shown in FIG. 19, an exemplary absorbent core storage component may contain no airfelt and therefore the component can be made relatively thinner and more flexible for the comfort of the wearer. In addition, the particles of the superabsorbent polymer can be immobilized relatively more easily in the absence of airfelt. As shown in FIG. 19, the layer 275 of the thermoplastic material intermittently contacts and adheres to a substrate sheet 274 at the areas of attachment 282. Between the areas of attachment 282, the layer 275 diverges away from the substrate sheet 274 to form the pockets 280. The layer 275 may have the form of a sheet of fibers of the thermoplastic material through which the liquid bodily waste may pass to be absorbed by the particles 270 of the superabsorbent polymer.

In FIG. 19, a separate thermoplastic layer covering sheet 276 is shown overlying the layer 275 of the thermoplastic material. Alternatively, the separate thermoplastic layer covering sheet 276 may be omitted. As another alternative, two absorbent core storage components each like that shown in FIG. 19 except for the omission of the thermoplastic layer covering sheet 276 may be superposed with one absorbent core storage component inverted such that the respective substrate sheets distally oppose each other. In such a combination of absorbent core storage components, either or both of the distally opposing substrate sheets may serve respectively as either or both of an upper covering sheet and a lower covering sheet for the absorbent assembly. Alternatively, the absorbent assembly may include a separate lower covering sheet that is disposed between the absorbent core and the interior surface of the chassis and/or a separate upper covering sheet that is disposed interiorly of the absorbent core.

Figure 20:
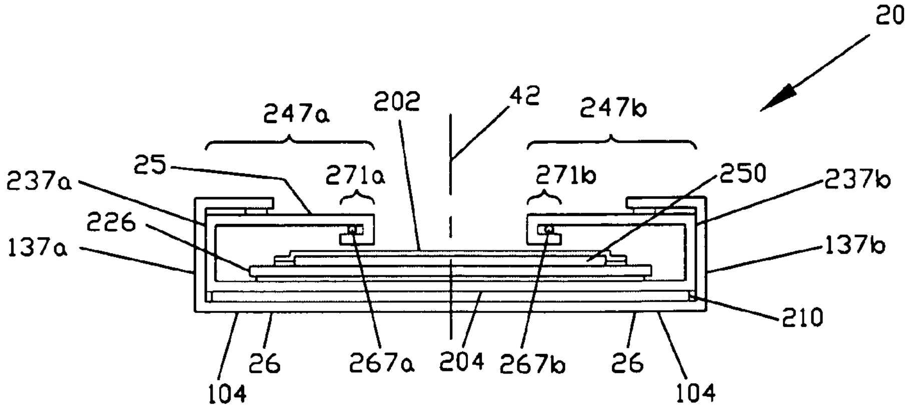
FIG. 20 is a section view of an exemplary absorbent assembly 200 having an additional bottom sheet 226.

The absorbent assembly may include an additional bottom sheet of a film or other water-impermeable material to enhance the protection against leakage. For example, as shown in FIG. 20, an additional bottom sheet 226 of a film or other water-impermeable material may be attached inside the absorbent assembly between the lower covering sheet 25 and the absorbent core 250. Alternatively, the bottom sheet may be attached to the absorbent assembly exteriorly of the lower covering sheet. This bottom sheet may extend laterally less far than either or both of the left side edge 237*a* and the right side edge 237*b* of the absorbent assembly 200, as shown in FIG. 20, or may extend laterally to overlap one or both of the side edges of the absorbent assembly.

The disclosures of all patents, patent applications and any patents which issue thereon, as well as any corresponding published foreign patent applications, and all publications listed and/or referenced in this description, are hereby incorporated herein by reference. It is expressly not admitted that any of the documents or any combination of the documents incorporated herein by reference teaches or discloses the present invention.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. A disposable diaper having a front waist region, a back waist region, and a crotch region between the waist regions and comprising:

an absorbent assembly having an interior surface and an exterior surface and laterally opposing longitudinally extending breathable side flaps, each side flap having longitudinally opposing ends and a longitudinally extending proximal edge, each side flap being attached adjacent to its ends to the interior surface of the absorbent assembly and having a longitudinally extending elastic gathering member attached adjacent to its proximal edge such that when allowed to relax, the elastic gathering member contracts and lifts the proximal edge away from the interior surface of the absorbent assembly, thereby raising the side flap to form a breathable side barrier; and a chassis attached to the exterior surface of the absorbent assembly and having an interior surface and an exterior surface and including a water-impermeable backsheet, wherein at least a portion of the chassis is extensible and wherein laterally opposing portions of the chassis in the crotch region are folded laterally inward to overlap the respective side flaps and are attached to the respective side flaps.

2. The disposable diaper of claim 1 wherein the extensible portion of the chassis includes at least two distinct laterally extending embossed regions each containing a pattern of generally longitudinally oriented alternating ridges and valleys created by an embossment and also containing an unembossed region located between the embossed regions, such that the portion of the chassis can be laterally extended to a given extent with the application of relatively less force than that required to laterally extend the same portion of the chassis to the same given extent before the embossment.

3. The disposable diaper of claim 1 wherein the extensible portion of the chassis underlies the absorbent assembly in one of the waist regions and is laterally extensible.

4. The disposable diaper of claim 1 wherein the extensible portion of the chassis is disposed in one of the waist regions and is laterally extensible to a greater degree than at least a portion of the chassis in the crotch region.

5. The disposable diaper of claim 1 wherein the laterally opposing laterally inwardly folded portions of the chassis overlap the respective side flaps less far laterally inward than the respective proximal edges of the respective side flaps and thereby leave uncovered respective exposed portions of the respective side flaps adjacent to the proximal edges.

6. The disposable diaper of claim 1 wherein the absorbent assembly is attached to the chassis in a cruciform pattern of attachment.

7. The disposable diaper of claim 1 further comprising cohesive fastening elements disposed on both an interior surface of the disposable diaper and an exterior surface of the disposable diaper such that the front waist region may be fastened over the back waist region or the back waist region may alternatively be fastened over the front waist region to encircle a waist and a leg of a wearer.

8. The disposable diaper of claim 1 wherein the absorbent assembly has a length smaller than a length of the chassis.

9. The disposable diaper of claim 1 wherein the absorbent assembly includes an absorbent core and a water-impermeable lower covering sheet disposed exteriorly of the absorbent core.

10. The disposable diaper of claim 9 wherein the absorbent assembly also includes a water-impermeable bottom sheet disposed between the lower covering sheet and the absorbent core.

11. The disposable diaper of claim 1 wherein the absorbent assembly includes an absorbent core storage component.

12. The disposable diaper of claim 11 wherein the absorbent core storage component contains no airfelt.

13. The disposable diaper of claim 11 wherein the absorbent assembly includes an absorbent core acquisition component.

14. The disposable diaper of claim 13 wherein the absorbent core acquisition component has a length smaller than a length of the absorbent core storage component and is disposed longitudinally offset from the absorbent core storage component.

15. The disposable diaper of claim 1 wherein the chassis includes at least one fastening element adapted for fastening the front waist region and the back waist region together to encircle a waist and legs of a wearer.

16. A disposable diaper having a front waist region, a back waist region, and a crotch region between the waist regions and comprising:

an absorbent assembly having an interior surface and an exterior surface and laterally opposing longitudinally extending breathable side flaps, each side flap having longitudinally opposing ends and a longitudinally extending proximal edge, each side flap being attached adjacent to its ends to the interior surface of the absorbent assembly and having a longitudinally extending elastic gathering member attached adjacent to its proximal edge such that when allowed to relax, the elastic gathering member contracts and lifts the proximal edge away from the interior surface of the absorbent assembly, thereby raising the side flap to form a breathable side barrier, wherein the absorbent assembly comprises an absorbent core storage component containing no airfelt; and a chassis attached to the exterior surface of the absorbent assembly and having an interior surface and an exterior surface and including a water-impermeable backsheet, wherein laterally opposing portions of the chassis in the crotch region are folded laterally inward to overlap the respective side flaps and are attached to the respective side flaps.

* * * * *

UNITED STATES PATENT AND TRADEMARK OFFICE

CERTIFICATE OF CORRECTION

PATENT NO. : 7,318,820 B2
APPLICATION NO. : 10/799947
DATED : January 15, 2008
INVENTOR(S) : Gary Dean LaVon et al.

It is certified that error appears in the above-identified patent and that said Letters Patent is hereby corrected as shown below:

Column 3
Line 23, delete "+45" and insert --±45--.

Column 4
Line 61, delete "clot-like" and insert --cloth-like--.

Signed and Sealed this

Tenth Day of June, 2008

JON W. DUDAS
*Director of the United States Patent and Trademark Office*